United States Patent [19]
McVenes et al.

[11] Patent Number: 5,964,795
[45] Date of Patent: Oct. 12, 1999

[54] MEDICAL ELECTRICAL LEAD

[75] Inventors: Rick D. McVenes, Isanti; Vicki L. Bjorklund, Maple Grove, both of Minn.

[73] Assignee: Medtronic, Inc., Minneapolis, Minn.

[21] Appl. No.: 09/042,286

[22] Filed: Mar. 13, 1998

[51] Int. Cl.⁶ ...................................................... A61N 1/05
[52] U.S. Cl. ............................................................ 607/122
[58] Field of Search .................................. 607/121, 122, 607/127, 128, 131, 123

[56] References Cited

U.S. PATENT DOCUMENTS

| | | |
|---|---|---|
| 4,106,512 | 8/1978 | Bisping . |
| 4,280,512 | 7/1981 | Karr et al. . |
| 4,394,866 | 7/1983 | Hughes . |
| 4,402,328 | 9/1983 | Doring . |
| 4,402,330 | 9/1983 | Lindemans . |
| 4,454,888 | 6/1984 | Gold . |
| 4,458,677 | 7/1984 | McCorkle, Jr. . |
| 4,475,560 | 10/1984 | Tarjan et al. . |
| 4,497,326 | 2/1985 | Curry . |
| 4,506,680 | 3/1985 | Stokes . |
| 4,627,439 | 12/1986 | Harris . |
| 4,641,656 | 2/1987 | Smits . |
| 5,165,403 | 11/1992 | Mehra . |
| 5,246,014 | 9/1993 | Williams et al. . |
| 5,282,844 | 2/1994 | Stokes et al. . |
| 5,324,321 | 6/1994 | Pohndorf et al. . |
| 5,387,233 | 2/1995 | Alferness et al. . |
| 5,423,772 | 6/1995 | Lurie et al. . |
| 5,683,445 | 11/1997 | Swoyer . |

*Primary Examiner*—Scott M. Getzow
*Attorney, Agent, or Firm*—Reed A. Duthler; Harold R. Patton

[57] ABSTRACT

A cardiac pacing lead and a method of its use. The lead has an elongated insulative lead body having a distal section formed into a curved configuration appropriate for use in a coronary sinus/cardiac vein of a patient's heart. An active fixation device is located proximal to the distal, curved section of the lead body, which carries an electrode, located along the distal portion of the lead body, spaced from the active fixation device a distance appropriate to locate the electrode adjacent the left atrium or left ventricle of a human heart when the fixation device is located adjacent the ostium of the coronary sinus. The lead is used by advancing the distal portion of the lead through the coronary ostium of the patient's heart and into the coronary sinus/cardiac vein and therefter employing the active fixation device to affix the lead to the patients heart outside of the coronary sinus/cardiac vein.

11 Claims, 6 Drawing Sheets

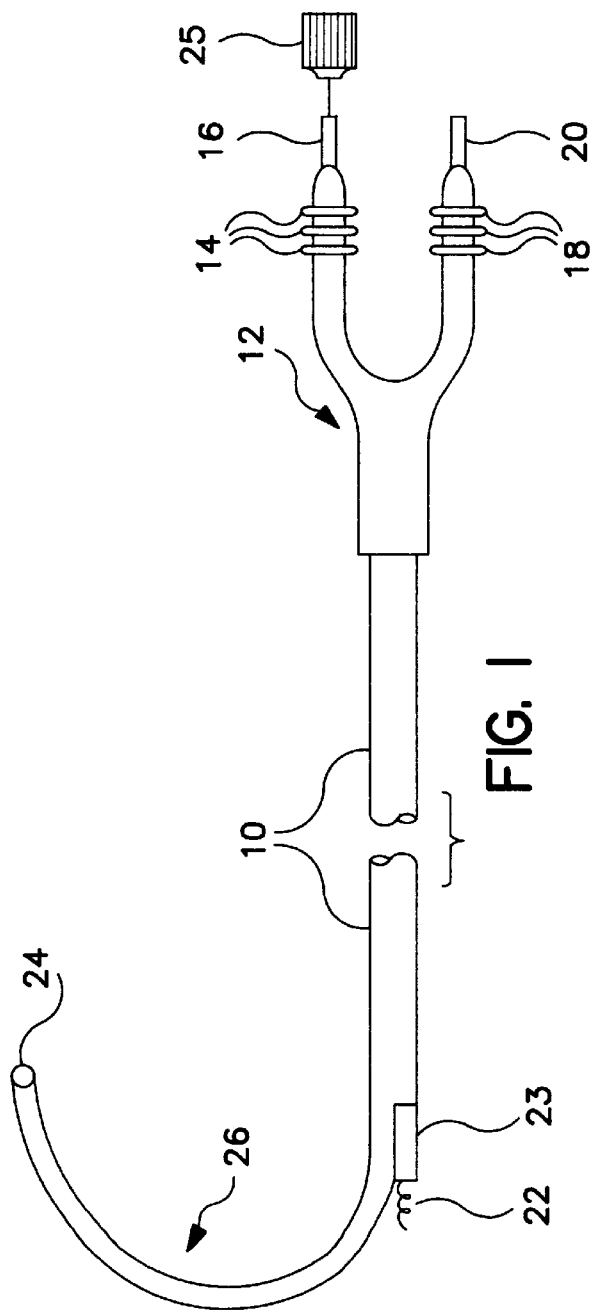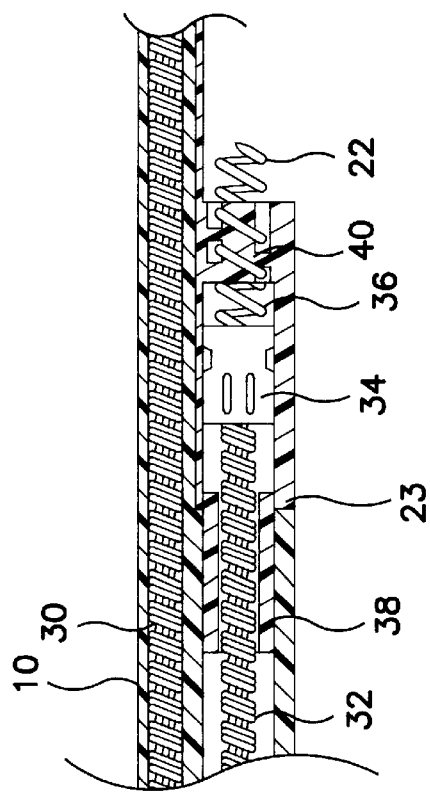

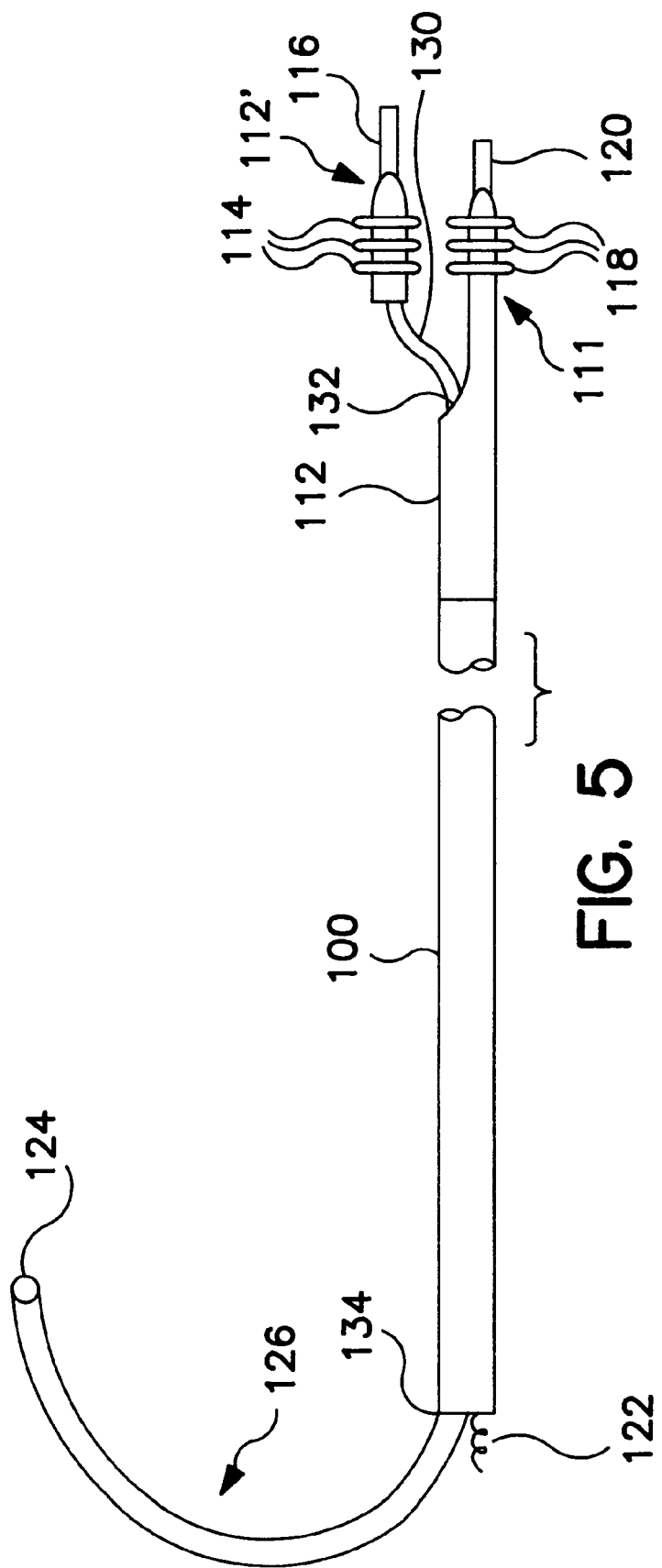

MEDICAL ELECTRICAL LEAD

BACKGROUND OF THE INVENTION

The present invention relates to electrical medical leads generally and more particularly to implantable cardiac pacing and defibrillation leads.

Over the years, numerous leads have been designed for the purpose of pacing the atria. One basic approach has been to provide the lead with a pre-formed "J"-shape, adapted to result in the electrode at the tip of the lead being reliably located in the right atrial appendage. Various approaches to providing a J-shaped lead have included the provision of molded, curved polyurethane lead bodies or sheaths as in U.S. Pat. No. 4,394,866 issued to Hughes and U.S. Pat. No. 4,627,439 issued to Harris, curved silicone rubber sheaths as in U.S. Pat. No. 4,402,328 issued to Doring, curved coils as in U.S. Pat. No. 4,402,330 issued to Lindemans, and curved reinforcing wires as in U.S. Pat. No. 4,454,888 issued to Gold. Such curve providing structures are incorporated in the distal portion of the lead so that it maintains a J-shaped configuration after implant, allowing the electrode to continue to resiliently engage the right atrial appendage until such time as it is anchored in place by means of fibrotic tissue growth.

Pacing the atria has also been accomplished by means of electrode leads located in the coronary sinus. One of the earlier coronary sinus leads is the Medtronic, Inc. Model 6992 Coronary Sinus Lead which has a generally straight lead body, carrying two ring electrodes. More recently, leads having pre-formed curved configurations have been employed for pacing and/or mapping the electrical activity of the atria, including U.S. Pat. No. 5,423,772 issued to Lurie, U.S. Pat. No. 5,387,233 issued to Alferness et al., and pending, commonly assigned U.S. Pat. No. 5,683,445 to Swoyer for a "Medical Electrical Lead", incorporated herein by reference in its entirety. An additional design for a curved coronary sinus lead is disclosed in commonly assigned co-pending application No. 08/695,977, filed Jul. 17, 1997 by Sommer et al for a "Medical Electrical Lead", also incorporated herein by reference in its entirety. Coronary sinus leads have also been used to pace and sense the ventricle by advancing the electrode into the great cardiac vein and as part of implantable defibrillation lead systems.

SUMMARY OF THE INVENTION

The present invention is directed toward providing an optimized pacing lead for location in the coronary sinus/cardiac veins of the human heart. An electrode or electrodes is located along the distal portion of the lead, at a location or locations appropriate to place the electrode adjacent the left atrium and/or left ventricle, as may be desired. In one preferred embodiment, the lead is provided with a pre-shaped curve along its distal portion, adapted to assist insertion of the lead into the coronary sinus and to maintain the lead in the coronary sinus after implant.

In addition to or as an alternative to the provision of a pre-curved distal portion of the lead, the present invention also includes an active fixation device located proximal to the distal portion of the lead intended to be inserted into the coronary sinus and/or great cardiac vein. The fixation helix secures the lead at the point of entry into the coronary sinus, preventing dislodgment of the lead. The active fixation device may serve as an additional electrode allowing for bi-atrial pacing or atrial-ventricular pacing or both, depending on the number and location of electrodes located along the distal portion of the leads, or may simply serve as a fixation device. The active fixation device may be conductive or non-conductive and may take the form of a rotatable helix, an extendible barb or any other known active fixation mechanism employed in the context of implantable cardiac leads. The distance between the active fixation device and the electrode or electrodes located along the distal portion of the lead controls their position relative to the left atrium and/or left ventricle. Thus, leads intended to pace the left ventricle will have electrodes located further from the active fixation device, while leads intended to pace the left atrium will have electrodes located relatively closer to the active fixation device.

In an additional preferred embodiment of the lead, the distal section of the lead intended to be installed in the coronary sinus/great vein is slideably mounted with regard to the lead body and is advanceable and retractable from the lead body from the proximal end of the lead. By this mechanism, the degree to which the coronary sinus/great vein lead extends into the coronary sinus/great vein is adjustable. Alternatively, leads having multiple lengths and/or curvatures defined for the portion of the lead extending distally to the fixation device may also be employed in order to allow sensing and stimulation at different sites within the coronary sinus/cardiac veins. The distal section may take the form of a C-shaped curve or an L-shaped curve or may take the form of a generally straight lead segment extending distally from the active fixation device.

The lead is employed by advancing the distal portion of the lead into the right atrium and then into the coronary sinus, subsequently advancing the lead until the fixation device in the transition region of the lead reaches tissue adjacent the opening of the coronary sinus and thereafter engaging the active fixation device with right atrial tissue, thereby also maintaining the electrodes along the distal portion of the lead in their desired locations. The lead may then be employed for dual chamber atrial pacing, atrial-ventricular pacing, or both. If provided with a defibrillation electrode, the lead may also be employed for cardioversion and defibrillation.

BRIEF DESCRIPTION OF THE DRAWINGS

FIG. 1 is a plan view of a pacing lead according to a first embodiment of a lead according to the present invention.

FIG. 2 illustrates a cross-sectional view through the lead of FIG. 1.

FIG. 5 is a plan view of a pacing lead according to a second embodiment of a lead according to the present invention.

DETAILED DESCRIPTION OF THE PREFERRED EMBODIMENTS

Figure 3D:
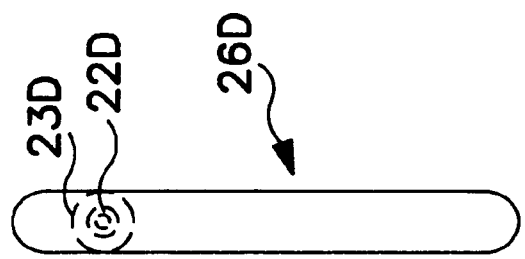
FIGS. 3A, 3B, 3C and 3D illustrate four alternative relationships between the pre-formed curve of the distal portion of the lead of FIG. 1 and the fixation device.

FIG. 1 is a plan view of a first embodiment of a lead according to the present invention. The lead is provided with an elongated insulative lead body 10 which carries therein an elongated conductor extending from distal electrode 24 to connector ring 16. This conductor may take the form of any known conductor employed in cardiac pacing leads, cardiac defibrillation leads, or the like. Also located within lead body 10 is a torque transfer means which may take the form of an elongated coiled conductor coupling helix 22 to connector pin 20. In a preferred embodiment of the invention, rotation of connector pin 20 causes rotation of the coiled conductor within the lead body to cause advancement and rotation of fixation helix 22 out of electrode head 23, precisely as disclosed in U.S. Pat. No. 4,106,512 issued to Bisping, incorporated herein by reference in its entirety.

Fixation helix 22 may be electrically coupled to connector pin 20 and employed as an electrode. Alternatively, fixation helix 22 may be insulated from connector pin 20 and employed simply as a fixation device. Fixation helix 22 may also be fabricated of a non-conductive rigid plastic material such as nylon and be employed solely as a fixation device. The distal, section 26 of the lead body may be "C" shaped as illustrated, or may correspond to the generally "C" shaped distal, curved sections in either the above cited Summers et al or the above cited Swoyer et al applications incorporated by reference above. Alternatively, the distal section 26 may take the form of an L-shaped curve as disclosed in U.S. Pat. No. 4,458,677 issued to McCorkle, also incorporated herein by reference in its entirety or may have a generally straight configuration. Electrode 24 may take the form of any conventional cardiac pacing electrode, and for example, may be a porous, sintered, steroid eluting electrode as disclosed in U.S. Pat. No. 4,506,680 issued to Stokes or U.S. Patent No. 5,282,844 issued to Stokes et al., both incorporated herein by reference in their entireties. The outer diameter of the electrode 24 may optionally be greater than the outer diameter of the distal portion 26. Electrode 24 may also correspond to the pacing/sensing electrodes disclosed in the above cited Sommer or Swoyer applications.

Connector pin 16 and connector pin 20 are mounted to bifurcated connector assembly 12. Sealing rings 14 and 18 seal the connector assembly within the bores of an associated cardiac pacemaker or other implantable device. In the specific embodiment illustrated, connector pin 16 is coupled to electrode/fixation device 22 by means of an elongated coiled conductor located in one of two lumens within lead body 10, according to the basic mechanism disclosed in the above-cited Bisping patent. While not illustrated, it is within the scope of the invention that the distal section 26 of the lead may include an elongated defibrillation electrode as a substitute for or in addition to pacing electrode 24.

In use, the distal section of the lead 26 if curved may be straightened by means of a stylet 25 inserted down the length of the lead body in a conventional fashion as advanced to a point adjacent the opening of the coronary sinus. The stylet is then slightly withdrawn proximally, allowing the lead body to display a curvature which assists in inserting the curved section 26 of the lead into the coronary sinus. If the distal section of the lead is generally straight in configuration, a curved stylet inserted along its length may be used to induce a curve in the distal portion and assist its insertion into the coronary sinus. The lead is advanced within the coronary sinus until the active fixation device 22 is adjacent the ostium of the coronary sinus and the active fixation device is employed to affix the lead to heart tissue adjacent the ostium.

FIG. 2 illustrates a cross-sectional view through the region of the lead carrying the fixation device/electrode 22. In this view it can be seen that the lead body is provided with first and second lumens carrying first and second conductors 30 and 32, respectively. In this view, both conductors take the form of elongated multifilar coils, typical of present cardiac pacing leads. In the embodiment illustrated, conductor 32 is rotatable within lead body 10 and coupled to fixation device/electrode 22 by means of a crimp sleeve 34. Rotation of conductor 32 causes advancement of fixation device/electrode 22 out the distal end of plastic electrode head 23, by interengagement with the guide portion 40 of the electrode head 23 in a conventional fashion. Also illustrated is a radiopaque marker ring 36, also conventional in present screw-in leads. The proximal portion 38 of the electrode head 23 is fabricated of a separate plastic member, and inserted in the distal end of the second lumen of lead body 10. The stylet 17 is passed down the interior lumen defined by coiled conductor 30, whereby the stylet may be advanced to the distal end of section 26 of the lead, and may thereby be used to either straighten the lead or to provide a curvature different from that pre-formed in distal section 26.

Figure 3C:
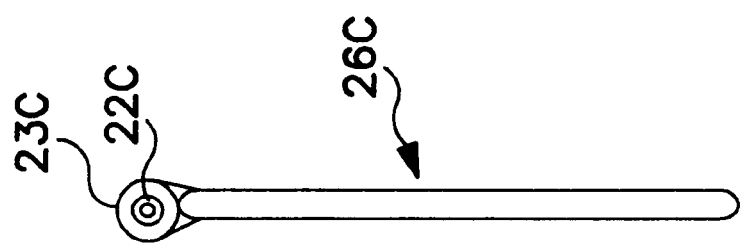
Figure 3B:
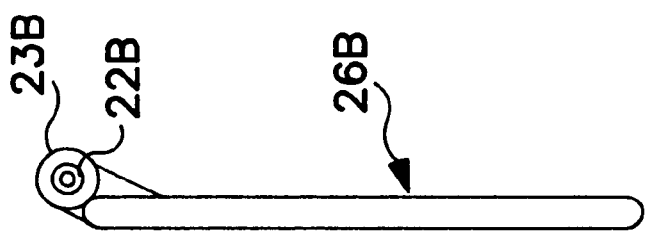
Figure 3A:
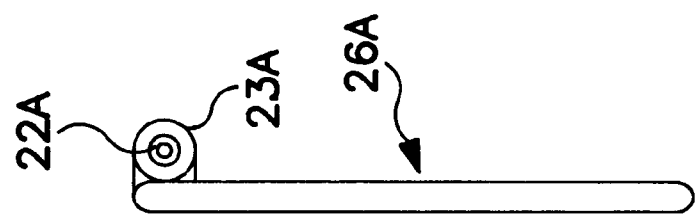

As illustrated in FIG. 1, the electrode head 23 is located along the interior portion of the pre-formed curve of the distal section 26 of the lead. However, the electrode head and associated fixation device/electrode 24 may be located in other orientations as well. FIGS. 3A, 3B and 3C illustrate three alternative relationships between the pre-formed curve of the distal section 26 of the lead and the electrode head 23. All three figures view the lead looking proximally along the main axis of the lead body proximal to the distal, from a point distal to the curve distal section.

In FIG. 3A, the electrode head 23A, carrying fixation device/electrode 22A is located at approximately a 90 degree angle to the plane in which curved distal section 26A lies. In FIG. 3B, electrode head 23B and fixation device/electrode 22B are located approximately 45 degrees displaced from the plane in which curved, distal section 26B is located. In FIG. 3C, electrode head 23C carrying fixation device/electrode 22C is located in the plane in which curved distal section 26C is located. However, in this case the electrode head 23C is located along the outside of the curve, rather than the inside of the curved distal section as in FIG. 1. FIG. 3D illustrates the configuration of the lead of FIG. 1, for the sake of comparison, with electrode head 23 and fixation device 22 located on the interior of curved section 26.

Figure 4A:
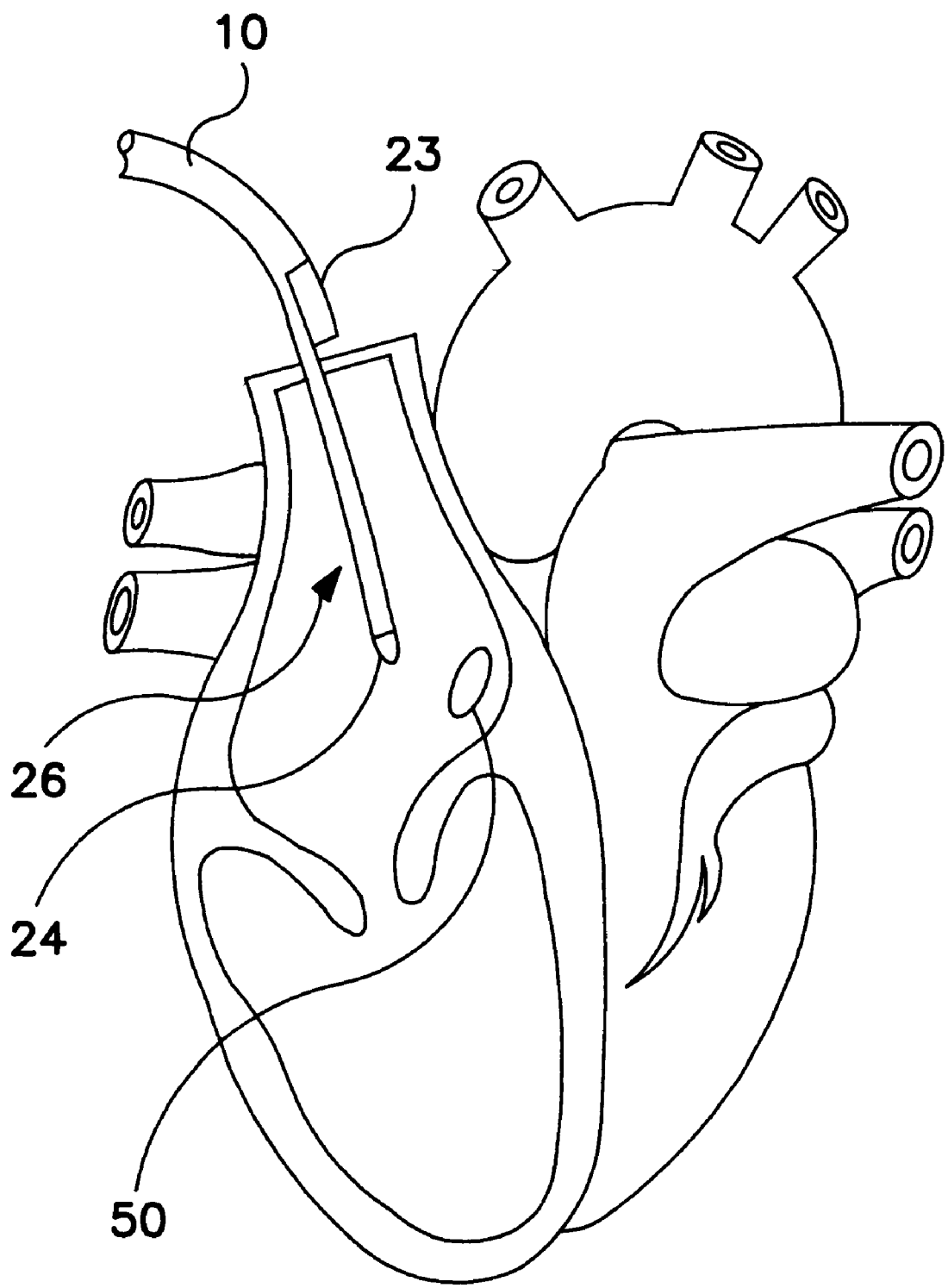
FIGS. 4A, 4B and 4C illustrate the method of the use of the lead of FIG. 1.
Figure 4B:
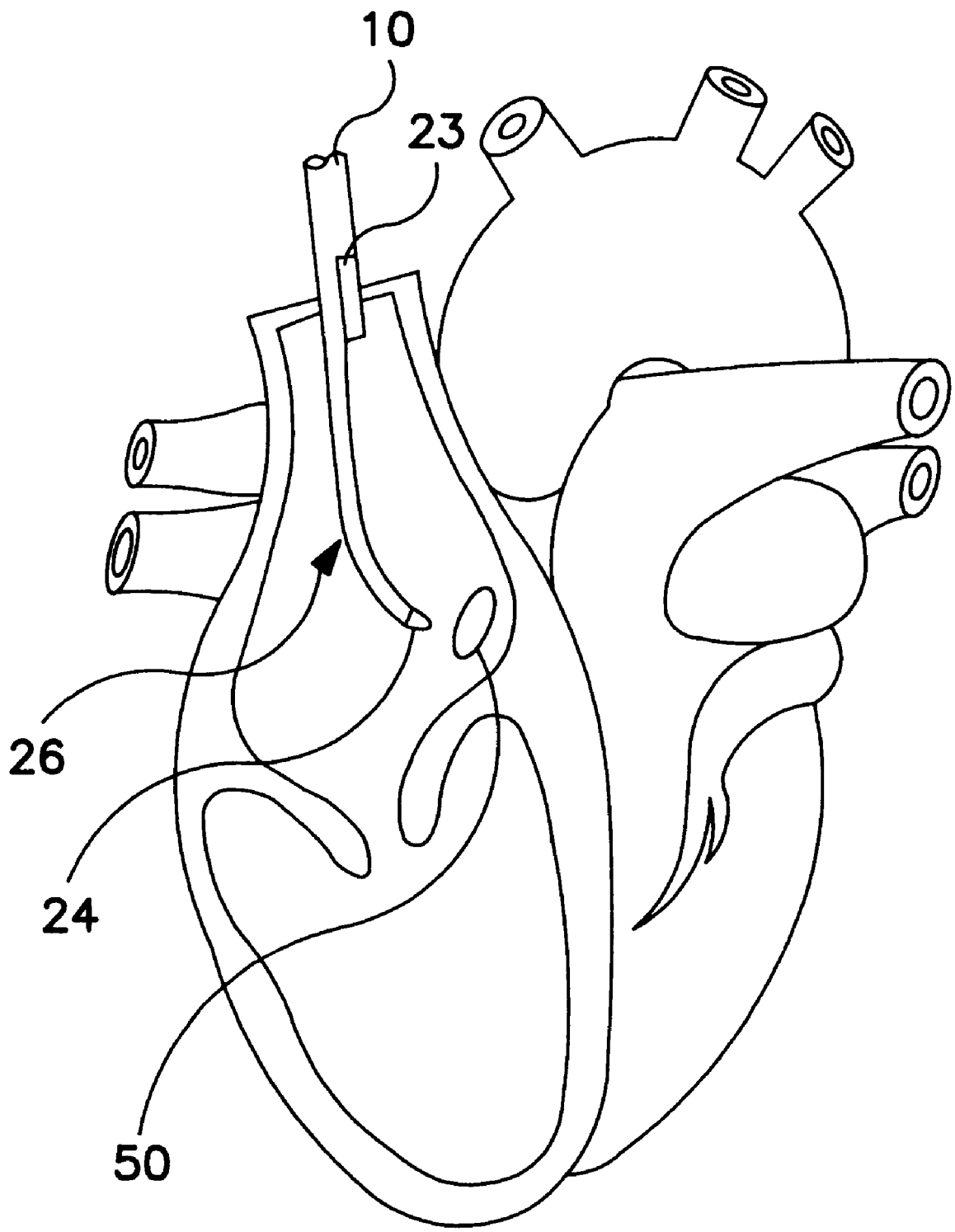
Figure 4C:
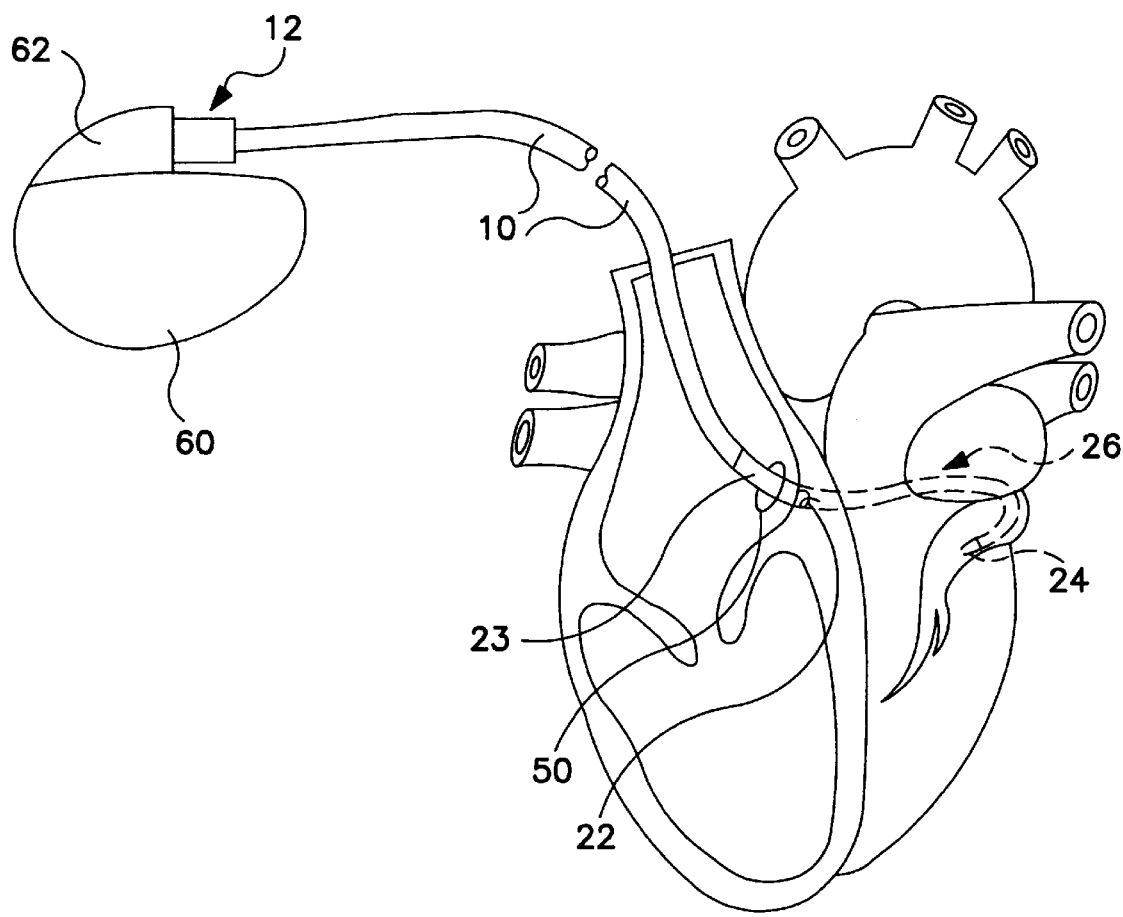

FIGS. 4A through 4C illustrate the method of the use of the lead. In FIG. 4A the lead body is advanced such that the distal portion of the lead 26 is located in the right atrium. As illustrated, the distal portion 26 of the lead has been straightened by means of a stylet, so that it can be advanced through the vascular system, and the active fixation device/electrode 24 has been withdrawn into electrode head 23 so as not to snag on vascular tissue during advancement of the lead. The lead is advanced until the electrode 24 is located in the general vicinity of the ostium 50 of the coronary sinus.

In FIG. 4B, the stylet has been withdrawn proximally slightly, so that the distal portion of distal section 26 exhibits a portion of its pre-curved configuration. The lead is then advanced and/or rotated to place electrode 24 into the ostium 50 of the coronary sinus. The lead is thereafter advanced into the coronary sinus, until the distal end of electrode head 23 lies in a desired position against atrial tissue adjacent to the ostium 50 of the coronary sinus. The fixation device/electrode 22 may then be slightly advanced in order to map the area adjacent the ostium coronary sinus to choose a desired location with adequate pacing and/or sensing thresholds. Mapping of the area adjacent the coronary sinus can be accomplished by rotating the lead around the stylet, and/or withdrawing the stylet proximally to about the location of the electrode head 23 and using the stylet to move the electrode head 23 round the tissue adjacent the ostium 50 of the coronary sinus until a desired location is found.

FIG. 4C illustrates the lead as finally implanted. After locating a desired position for fixation device/electrode 24, it is screwed out of the distal end of electrode 23 and into right atrial tissue, thus securing its location as well as the location of electrode 24 and any other electrodes located along the lead. The lead is then coupled to an implantable pacemaker 60 by insertion of connector assembly 12 into connector block 62 associated therewith. The pacemaker may then be employed to provide bi-atrial pacing, A-V pacing, or some combination of both types of pacing. In the specific embodiment illustrated in FIG. 4C, electrode 24 is located adjacent the left ventricle, and the pacemaker so illustrated may be employed to provide A-V sequential pacing. In the event that a lead according to the present invention is to be employed to provide bi-atrial pacing in addition to or instead of A-V sequential pacing, an electrode would be located adjacent the left atrium of the heart in addition to or as an alternative to the location of electrode 24 as illustrated. It should also be understood that in the context of the present invention an additional lead may be located in the right ventricle in order to additionally provide for the possibility of bi-ventricular pacing using a lead according to the present invention.

While not so illustrated, the leads of the present invention may also be employed for cardioversion and defibrillation. For example, in the manner illustrated in U.S. Pat. No. 5,165,403 issued to Mehra and U.S. Pat. No. 4,641,656 issued to Smits, both incorporated herein by reference in their entireties. In such circumstances, an elongated electrode would be arranged along the distal portion 26 of the lead, and optionally an additional elongated electrode may be arranged along lead body 10 such that when the lead is located as illustrated in FIG. 4C, the additional electrode is located in the right atrium/superior vena cava or outside of the heart. In such a configuration, the lead may be employed to deliver atrial cardioversion and defibrillation shocks. The lead may also be used in conjunction with a right ventricular defibrillation electrode to alternatively or additionally deliver ventricular cardioversion and defibrillation pulses.

FIG. 5 is a plan view of an alternative embodiment of the present invention in which a first lead body component 100 is formed with an elongated internal lumen extending along the length of thereof. Located within this elongated lumen is a slideable, second lead body component comprising an insulated conductor 130 which may take the form of a conductive coil covered by an insulative sheath. Insulated conductor 130 extends out of the distal opening of the lumen within first lead body component 100 to form the distal, optionally curved section 126 of the lead. Insulated conductor 130 extends out of the proximal opening of the lead body 100 and extends to a first electrical connector assembly 112 which carries a connector pin 116, coupled to tip electrode 128 and which is provided with sealing rings 114 to seal the connector assembly within the connector block of an associated implantable device. A rotatable connector pin 120 is located at the proximal end of connector assembly 118 which is coupled by means of an internally extending coiled conductor to advanceable helical fixation device 122. Connector assembly 111 is provided with sealing rings 118 to seal the connector assembly against entry of fluids when inserted into the connector block of an associated implantable device.

Insulated conductor 130 is slideable within the lumen of lead body component 100 so that the distal portion 126 of the lead can be advanced and retracted providing for various spacings between the tip electrode 124 and the fixation helix 122. If the distal section 126 of insulated conductor 130 is curved, advancement or retraction of the insulated conductor 130 may also produce different curved configurations. The ability to slide insulated conductor 130 relative to the lead body 100 and fixation helix 122 assists in locating electrode 124 adjacent desired portions of the heart. For example, if it is desired to sense and pace in the left ventricle, the distal portion 126 of the insulative conductor 130 may be advanced fully out of lead body component 100 so that it can be located in the great cardiac vein adjacent the left ventricle. If, however, pacing the left atrium is desired, the insulated conductor may be moved proximally, pulling the distal portion 126 thereof proximally as well.

While the above described leads employ helical fixation devices, it should be understood that a lead according to the present invention may also employ alternative fixation devices such as hooks, darts, barbs or the like. Examples of alternative fixation devices are disclosed in U.S. Pat. No. 4,475,560 issued to Tarjan, U.S. Pat. No. 4,497,326 issued to Curry and U.S. Pat. No. 4,280,512 issued to Karr et al., all incorporated herein by reference in their entireties. In addition, while both conductors in the illustrated embodiment take the form of coiled conductors, stranded conductors or other known conductor forms as disclosed in U.S. Pat. No. 5,246,014 issued to Williams et al. or U.S. Pat. No. 5,324,321 issued to Pohndorf et al., for example, might be substitutable for one or more of the coiled conductors illustrated or used in addition to the coiled conductors illustrated, depending upon the number and arrangement of electrodes on the lead. As such, the above disclosed embodiment should be considered exemplary, rather than limiting, with regard to the scope of the claims which follow.

In conjunction with the above disclosure, we claim:

1. A method of positioning an electrode within a coronary sinus/cardiac vein of a patient's heart, comprising:
   advancing a lead having an elongated lead body carrying an active fixation device and having an electrode located on the lead body distal to the fixation device through a coronary ostium of the patient's heart and into the coronary sinus/cardiac vein of the patients heart; and
   employing the active fixation device to affix the lead to the patients heart outside of the coronary sinus/cardiac vein.

2. A method according to claim 1 wherein the step of employing the active fixation device to affix the lead to the patients heart comprises affixing the lead to the patient's heart adjacent the coronary ostium of the patient's heart.

3. A method according to claim 1 or claim 2 wherein the step of advancing a lead comprises advancing a lead having a conductive fixation device, further comprising the step of employing the fixation device as an electrode.

4. A method according to claim 1 or claim 2 wherein the step of advancing a lead comprises advancing a lead having a conductor slideably mounted in the lead body and carrying the electrode distal to the fixation device and sliding the conductor relative to the lead body to position the electrode at a desired location within the coronary sinus/cardiac vein of the patient's heart.

5. A method according to claim 1 or claim 2 wherein the advancing step also comprises advancing said electrode to a position adjacent the left atrium of the patient's heart.

6. A method according to claim 1 or claim 2 wherein the advancing step comprises advancing said electrode into a position adjacent the left ventricle of a patient's heart.

7. A cardiac pacing lead, comprising:
a first lead body component having an active fixation device located on a distal portion thereof and a second lead body component having a distal portion formed into a configuration appropriate for use in a coronary sinus/cardiac vein of a patient's heart and slideably mounted relative to said first lead body component;
a first electrode, located along said distal portion of said second lead body component, locatable adjacent the left atrium or left ventricle of a human heart when the fixation device is located adjacent the ostium of the coronary sinus of said human heart by sliding said first lead body component relative to said second lead body component; and
an elongated conductor, extending through said second lead body component and coupled to said first electrode.

8. A lead according to claim 7 further comprising a second conductor, coupled to said active fixation device and extending proximally within said first lead body component.

9. A lead according to claim 13 or claim 8 wherein said active fixation device comprises a fixation helix.

10. A lead according to claim 9 wherein said fixation device comprises a rotatable fixation helix.

11. A lead according to claim 7 or claim 8 wherein the distal portion of the second lead body component is curved and lies generally within a plane.

* * * * *